(12) United States Patent
Cho

(10) Patent No.: US 8,246,912 B2
(45) Date of Patent: Aug. 21, 2012

(54) OPTICAL DETECTING APPARATUS FOR A BIO-CHIP

(75) Inventor: Seong-ho Cho, Gwacheon-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 218 days.

(21) Appl. No.: 12/533,560

(22) Filed: Jul. 31, 2009

(65) Prior Publication Data

US 2010/0099583 A1     Apr. 22, 2010

(30) Foreign Application Priority Data

Oct. 20, 2008   (KR) .................. 10-2008-0102465

(51) Int. Cl.
*G01N 21/64* (2006.01)
*G01N 21/00* (2006.01)
*C40B 60/12* (2006.01)
*G01N 21/76* (2006.01)
*G01J 3/42* (2006.01)

(52) U.S. Cl. ............... 422/82.08; 422/82.05; 422/82.06; 422/82.07; 422/82.09; 422/82.11; 250/458.1; 250/461.1; 250/461.2; 435/288.7; 436/164; 436/172; 356/320; 356/326; 356/327; 356/328; 506/39

(58) Field of Classification Search .................. None
See application file for complete search history.

(56) References Cited

U.S. PATENT DOCUMENTS

| 5,631,141 | A | 5/1997 | Sonek et al. |
| 6,197,503 | B1 * | 3/2001 | Vo-Dinh et al. ................ 435/6 |
| 6,620,623 | B1 | 9/2003 | Yershov et al. |
| 6,919,201 | B2 | 7/2005 | Tanaami et al. |
| 2003/0031596 | A1 * | 2/2003 | Tanaami ................. 422/82.08 |
| 2004/0234417 | A1 | 11/2004 | Schienle et al. |

FOREIGN PATENT DOCUMENTS

| DE | 10145701 A1 | 4/2003 |
| DE | 102006023945 A1 | 11/2007 |
| KR | 1020030037314 A | 5/2003 |
| KR | 1020040000858 A | 1/2004 |
| KR | 1020050068809 A | 7/2005 |
| KR | 1020060058638 A | 5/2006 |
| KR | 100728897 B1 | 6/2007 |
| WO | 2007/135091 A2 | 11/2007 |

OTHER PUBLICATIONS

European Search Report for Application No. 09173240.4-1234/2177897 dated Apr. 16, 2010.
Girkin, et al., Use of adaptive optics for improved multiphoton imaging, Multiphoton Microscopy in the Biomedical Sciences IV, Proc. of SPIE vol. 5323, pp. 260-266. Jun. 21, 2004.
Korean Office Action with English Translation for Application No. 10-2008-0102465 dated Aug. 30, 2010.

* cited by examiner

*Primary Examiner* — Neil N Turk

(57) ABSTRACT

An optical detecting apparatus for a bio-chip, the optical detecting apparatus including: a light source system for illuminating a bio-chip with an excitation light; a fluorescent light detecting system for detecting a fluorescent light emitted by the bio-chip; and a light path altering unit for directing the excitation light emitted by the light source system to a bio-chip and directing the fluorescent light emitted by the bio-chip to the fluorescent light detecting system, wherein a cross-sectional area of the excitation light irradiated by the light source system onto the bio-chip is greater than an area of the bio-chip, and the fluorescent light detecting system detects a fluorescent image of the entire bio-chip with a single illumination of excitation light.

7 Claims, 7 Drawing Sheets

OPTICAL DETECTING APPARATUS FOR A BIO-CHIP

CROSS-REFERENCE TO RELATED APPLICATIONS

This application claims priority to Korean Patent Application No. 10-2008-0102465, filed on Oct. 20, 2008, and all the benefits accruing therefrom under 35 U.S.C. §119, the contents of which in its entirety are herein incorporated by reference.

BACKGROUND

1. Field

One or more embodiments relate to an optical detecting apparatus for a bio-chip.

2. Description of the Related Art

A bio-chip is a biopsy device similar to a semiconductor chip and may be formed by combining a biogenic organic compound, such as an enzyme, peptides, protein, antibody, or deoxyribonucleic acid ("DNA") of a living organism, microorganism, cell, or organ, or a nerve cell of an animal or plant, onto a small chip. A DNA chip is a device for detecting DNA, which is made by arranging single-strand DNAs having different nucleotide base sequences, of which functions within a cell are known, within a small space on a substrate, such as on a glass substrate or a semiconductor substrate. A collection of single-strand DNAs having the same nucleotide base sequence is generally referred to as a spot, and generally 20 to 150 bases are connected to form one spot.

When genetic material of a sample flows on such a DNA chip, only genes corresponding to a specific spot, that is genes having a complementary nucleotide base sequence with a nucleotide base sequence of the specific spot, are combined with the corresponding spot, and genes which are not combined with spots in the DNA chip do not bind and may be washed out. Functions of nucleotide base sequences of spots arranged on a DNA chip are already known, and thus genetic information of a sample can be obtained by identifying spots in the DNA chip combined with genes. Therefore, aspects of unique genetic expression and/or alteration such as single nucleotide polymorphism and copy number variation in a gene or mutation in specific cells or organic tissues can be analyzed with relative rapidity. Furthermore, DNA chips can also be used in analysis of genetic expression, infection tests of pathogenic bacteria, antibiotic-resistance tests, research on biological reactions with respect to environmental factors, food safety inspection, identification of criminals, development of new drugs and medical inspection of animals or plants.

Various methods for identifying spots in a DNA chip combined with genes have been suggested, and the most popular method in this regard is the fluorescent detection method. In the fluorescent detection method, a base carrying a fluorescent material, which emits light of a specific color when excited by an excitation light, is combined with genetic material of a sample. After genetic material flows on a DNA chip, an excitation light is irradiated onto the DNA chip, and a fluorescent image obtained therein is analyzed. Thus, spots combined with genes of the sample can be identified. For example, the size of the spots ranges from 1 μm to 100 μm.

Generally, an optical detecting apparatus for obtaining a fluorescent image by irradiating excitation light onto a DNA chip obtains a fluorescent image by scanning a DNA chip in pixels of approximately 0.1 micrometers ("μm") to 10 μm. Furthermore, hundreds to tens of millions of (e.g. 1,000) spots form an array in one DNA chip. Using a bio-chip scanner, that is a fluorescence detecting apparatus for reading an entire DNA chip by scanning each of spot arrays in the DNA chip, it takes a longer period of time to obtain a fluorescent image of higher resolution, and it generally takes approximately 10 minutes to read an entire DNA chip by scanning each of panels in the DNA chip. Furthermore, a longer period of time is necessary for converting a plurality of fluorescent images obtained from the scanning to information corresponding to original spots on the DNA chip.

SUMMARY

One or more embodiments include an optical detecting apparatus for a bio-chip, the optical detecting apparatus capable of reading an entire bio-chip with a single illumination, or a few illuminations of excitation light, instead of scanning, for example, a DNA chip.

Additional aspects, features and advantages will be set forth in part in the description which follows.

Disclosed is an optical detecting apparatus for a bio-chip, the optical detecting apparatus including a light source system for illuminating a bio-chip with an excitation light; a fluorescent light detecting system for detecting a fluorescent light emitted by the bio-chip; and a light path altering unit for directing the excitation light emitted by the light source system to a bio-chip and directing the fluorescent light emitted by the bio-chip to the fluorescent light detecting system, wherein a cross-sectional area of the excitation light irradiated by the light source system onto the bio-chip is greater than an area of the bio-chip, and the fluorescent light detecting system detects a fluorescent image of the entire bio-chip with a single illumination of excitation light.

The light source system may include a light source, a light diffusing device and a condenser lens or a condenser mirror, which are sequentially disposed on a same optical axis and in a direction in which the excitation light travels.

Furthermore, the light source system may include a light source emitting the excitation light, an optical fiber transmitting the excitation light and a condenser lens or a condenser mirror condensing the excitation light onto the bio-chip.

The light path altering unit may include a polarizing beam splitter disposed between the light diffusing device and the condenser lens or the condenser mirror, a polarizer disposed between the light diffusing device and the polarizing beam splitter, and a quarter-wave plate disposed between the polarizing beam splitter and the condenser lens or the condenser mirror.

Alternatively, the light path altering unit may be a dichromic mirror disposed between the light diffusing device and the condenser lens or the condenser mirror.

Furthermore, the fluorescent light detecting system may include an excitation light absorbing filter, a deformable mirror, a projection optical system and an optical detector, which are sequentially disposed in a direction in which the fluorescent light travels, and the excitation light absorbing filter may be disposed to face a fluorescent light outputting surface of the polarizing beam splitter.

In an embodiment, the deformable mirror includes a reflective surface, which can be deformed by mechanical or electrical manipulation to correct for a distortion in the fluorescent image.

In an embodiment, the projection optical system may be a zoom lens system or a zoom mirror system, having variable magnification.

The optical detector includes an array of pixels, and may be a photo multiplier tube ("PMT"), a charge-coupled device, ("CCD"), a complementary metal-oxide semiconductor image sensor ("CIS CMOS") or a combination thereof.

An image of a single gene spot within a bio-chip may be matched to at least one of the pixels of the optical detector.

The optical detecting apparatus may further include a stage for supporting, moving, tilting and rotating the bio-chip.

To achieve the above and/or other aspects, features or advantages one or more embodiments include an optical detecting apparatus for a bio-chip, the optical detecting apparatus including a light source system for illuminating a bio-chip with an excitation light; and a fluorescent light detecting system for detecting a fluorescent light emitted by the bio-chip, wherein the light source system and the fluorescent light detecting system are disposed on the opposite sides of a bio-chip, a cross-sectional area of the excitation light irradiated by the light source system onto the bio-chip is greater than an area of the bio-chip, and the fluorescent light detecting system detects a fluorescent image of the entire bio-chip with a single illumination of the excitation light.

The light source system may further include a collimating lens or a collimating mirror disposed between the light diffusing device and the condenser lens or the condenser mirror.

A cross sectional area of a light spot focused by the condenser lens or the condenser mirror onto the bio-chip may be greater than an area the entire bio-chip.

The fluorescent light detecting system may include an excitation light absorbing filter, a deformable mirror, a projection optical system and an optical detector, which are sequentially disposed in a direction in which the fluorescent light travels, and the excitation light absorbing filter may be disposed to face a fluorescent light outputting surface of the polarizing beam splitter.

Alternatively, the fluorescent light detecting system may include an excitation light absorbing filter and an optical detector, which are integrated with a bio-chip to form a single body and are fixed on a surface of the bio-chip, which is a surface opposite to a surface of the bio-chip illuminated by excitation light.

The light source system may include a light source, a light diffusing device, a condenser lens or a condenser mirror and an aberration compensating device, which are sequentially disposed on a same optical axis and a direction in which the excitation light travels.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
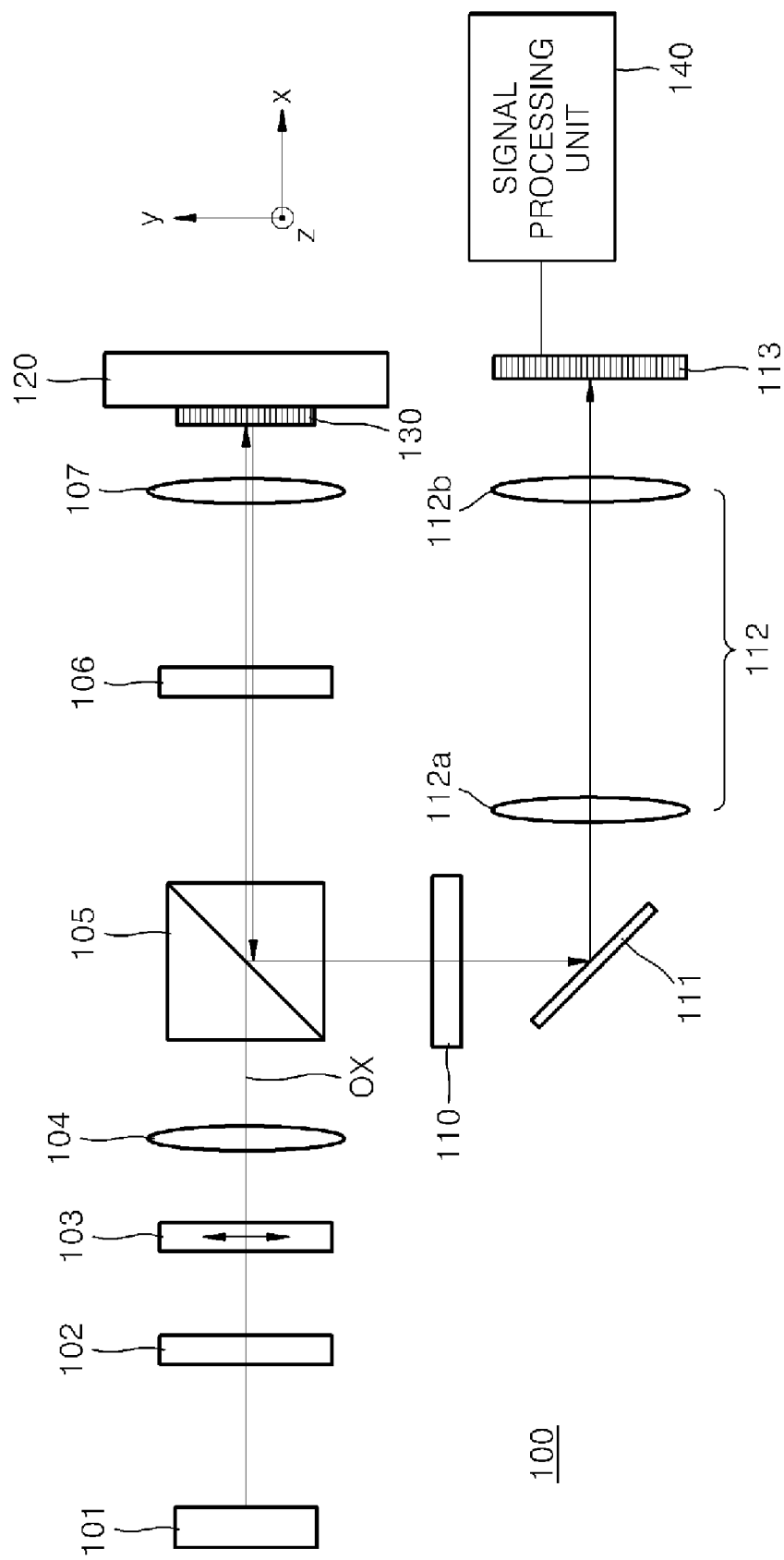
FIG. 1 is a diagram schematically showing an exemplary embodiment of an optical detecting apparatus for a bio-chip.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are described below, with reference to the figures, to explain aspects, features and advantages of the present description.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

It will be understood that, although the terms first, second, third, etc., can be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer, or section discussed below could be termed a second element, component, region, layer, or section without departing from the teachings of the exemplary embodiments of the invention.

Spatially relative terms, such as "below," "lower," "upper" and the like, can be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device can be otherwise oriented (rotated 90 degrees or at other orientations) and the spatially relative descriptors used herein interpreted accordingly.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation can result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

FIG. 1 is a diagram schematically showing an exemplary embodiment of an optical detecting apparatus 100 for a bio-chip. Referring to FIG. 1, the optical detecting apparatus 100 includes a light source 101, a light diffusing device 102, a polarizer 103, a collimating lens 104, a polarizing beam splitter 105, a quarter-wave ("λ/4") plate 106 and a condenser lens 107 disposed in a direction in which an excitation light travels along an optical axis OX, and further includes an excitation light absorbing filer 110, a deformable mirror 111, a projection optical system 112 and an optical detector 113 disposed in a direction in which a fluorescent light travels. In an embodiment, the optical detecting apparatus 100 includes a light source 101, a light diffusing device 102, a polarizer 103, a collimating lens 104, a polarizing beam splitter 105, a quarter-wave ("λ/4") plate 106 and a condenser lens 107 sequentially disposed in a direction in which an excitation light travels along an optical axis OX, and further may include an excitation light absorbing filer 110, a deformable mirror 111, a projection optical system 112 and an optical detector 113 sequentially disposed in a direction in which a fluorescent light travels. The configuration of the optics may vary according to a design of the optical detecting apparatus. In an embodiment, the light source 101, the light diffusing device 102, the collimating lens 104 and the condenser lens 107 constitute a light source system for illuminating a bio-chip 130. Furthermore, the excitation light absorbing filter 110, the deformable mirror 111, the projection optical system 112 and the optical detector 113 form a fluorescent light detecting system. Furthermore, the polarizer 103, the polarizing beam splitter 105 and the λ/4 plate 106 form a light path altering unit.

Although the optical system disclosed in the current embodiment and other embodiments below are refraction optical systems, comprising lenses, the same effects may be obtained using a reflection optical system, which includes a concave mirror or a convex mirror, instead of a refraction optical system. For example, instead of a condenser lens, a collimating lens and a zoom lens system, a condenser mirror, a collimating mirror and a zoom mirror system may be used. Furthermore, a reflection-refraction optical system including both a refraction lens and a reflection mirror may also be used. For clarity, the description below discloses a refraction optical system.

In a light source system, the light source 101 emits an excitation light. The excitation light is a light for exciting a fluorescent material in sample genes combined with a spot within a bio-chip 130 (e.g. a DNA chip). For example, light having a wavelength between about 200 nanometers ("nm") and about 2000 nm, specifically between about 350 nm and about 650 nm, more specifically about 540 nm may be used as excitation light. In an embodiment, light emitted by the light source 101 does not have to be monochromatic light having a wavelength of about 540 nm, and may be any light as long as the light includes light having a wavelength of about 540 nm. Furthermore, a wavelength of the excitation light may vary according to characteristics of the fluorescent material, for example. Therefore, the light source 101, which emits excitation light, may be, for example, a lamp emitting white light, a light emitting diode ("LED") or a laser diode ("LD") emitting monochromatic light having a wavelength of about 540 nm. Furthermore, excitation light may be either coherent light or incoherent light, for example. Also, light emitted by the light source 101 may be polarized light or unpolarized light.

The excitation light emitted by the light source 101 may pass through the light diffusing device 102. The light diffusing device 102 evenly diffuses the excitation light such that light output from the light diffusing device 102 has uniform intensity over its cross-section. The reason that the excitation light desirably has uniform intensity is to irradiate light of the same intensity onto the entire bio-chip 130. The irradiation of light of the same intensity may be important to ensure reliability of detected data. Although the light diffusing device 102 is shown as a flat-panel device in FIG. 1, the present embodiments are not limited thereto, and the light diffusing device 102 may be variously configured. For example, the light diffusing device 102 may be a stick-shaped light integrator. In another embodiment, the light diffusing device 102 may comprise a plurality of optical devices in order to improve uniformity of the excitation light.

Figure 2:
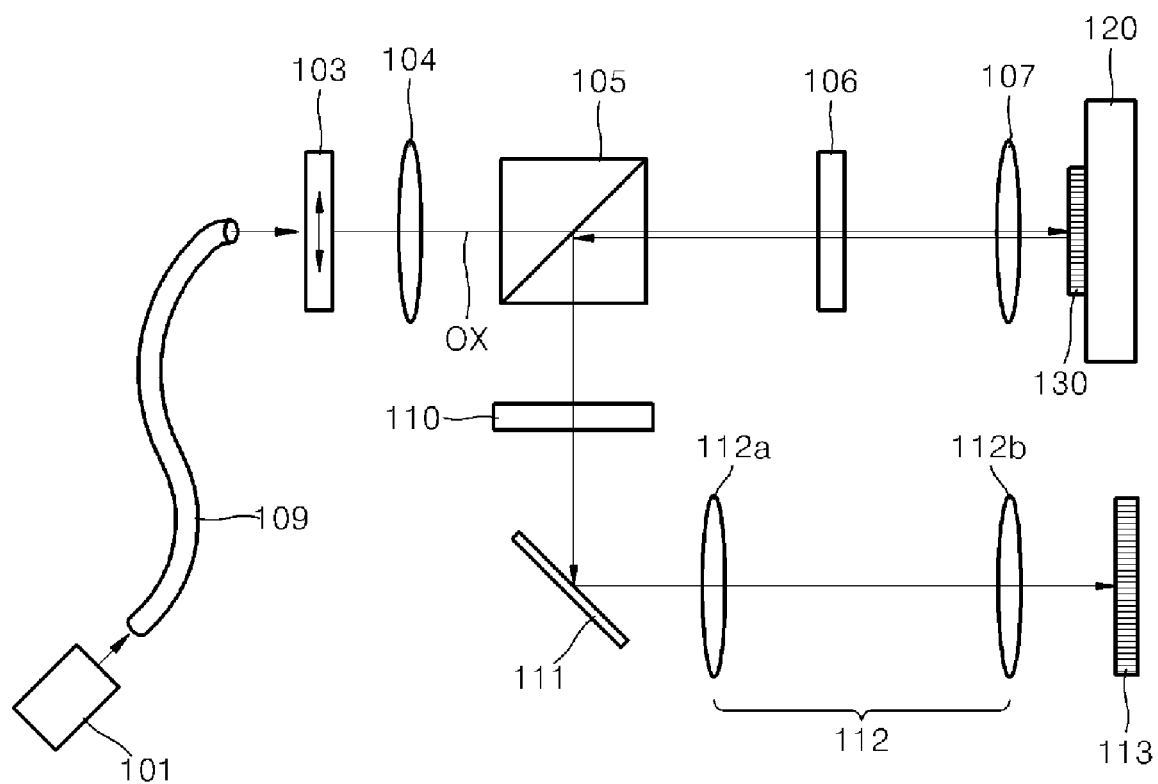
FIG. 2 is a diagram schematically showing another exemplary embodiment of an optical detecting apparatus for a bio-chip.

Furthermore, although the light source 101 and the light diffusing device 102 are disposed on the optical axis OX in FIG. 1, in another embodiment, the light source 101 and the light diffusing device 102 may be disposed off the optical axis OX, for example in an embodiment where a light transmitting or guiding device, e.g. an optical fiber 109 (refer to FIG. 2), is used. As shown in FIG. 2, in an embodiment using the optical fiber 109, excitation light may be diffused to have sufficient uniformity while the excitation light travels inside the optical fiber 109, and thus in an embodiment the light diffusing device 102 of FIG. 1 may be omitted. Furthermore, in an embodiment using the optical fiber 109, the degree of freedom with respect to layout designs of the light source 101 may be improved, and effort for aligning the light source 101 during assembly of the optical detecting apparatus 100 may be reduced.

The polarizer 103 may be disposed after the light diffusing device 102 (or an optical fiber (not shown)). In an embodiment, the polarizer 103 is disposed after the light diffusing device 102. The polarizer 103 acts such that an excitation light has a specific polarization. For example, the excitation light, which passes through the polarizer 103, may have S-polarization. However, in an embodiment where the light source 101 is configured to emit light of a specific polarization, the polarization 103 may be omitted.

Optionally, excitation light, having passed through the polarizer 103, may pass through the collimating lens 104. The collimating lens 104 converts excitation light to parallel light. Although the collimating lens 104 is disposed after the polarizer 103 in FIG. 1, the collimating lens 104 may also be disposed between the light source 101 and the light diffusing device 102 or between the light diffusing device 102 and the polarizer 103. However, in an embodiment where the divergence of excitation light emitted by the light source 101 is not large and the excitation light may be sufficiently condensed by the condenser lens 107, the collimating lens 104 may be omitted.

The polarizing beam splitter 105 may be disposed after the collimating lens 104. In another embodiment, the polarizing beam splitter 105 is disposed after the collimating lens 104. The polarizing beam splitter 105 either reflects or transmits incident light according to a polarization of the incident light. For example, the polarizing beam splitter 105 may transmit light of S-polarization and reflect light of P-polarization. By using the polarizing beam splitter 105, the excitation light emitted by the light source 101 may be directed to the bio-chip 130 and the light reflected by the bio-chip 130 may be directed to the optical detector 113. In this regard, the polarizing beam splitter 105 may be considered as a light path altering device. As described above, the polarizing beam splitter 105 forms a light path altering unit together with the polarizer 103 and the λ/4 plate 106, and principles thereof are described in further detail below. FIG. 1 shows that excitation light emitted by the light source 101 passes through the polarizing beam splitter 105 and travels to the bio-chip 130 and light reflected by the bio-chip 130 is reflected by the polarizing beam splitter 105. However, in another embodiment, the apparatus may be configured such that the excitation light emitted by the light source 101 is reflected by the polarizing beam splitter 105 and the light reflected by the bio-chip 130 passes through the polarizing beam splitter 105. In this embodiment, instead of the λ/4 plate 106, the condenser lens 107 and the bio-chip 130, the excitation light absorbing filter 110, the deformable mirror 111, the projection optical system 112 and the optical detector 113 may be disposed on the optical axis OX.

The excitation light, having passed through the polarizing beam splitter 105, may pass through the λ/4 plate 106. The λ/4 plate 106 converts light of linear polarization to light of circular polarization or vice versa. For example, light of S-polarization incident to the λ/4 plate 106 may be converted to light of left-circular polarization.

Next, the excitation light, which is converted to light of circular polarization, is incident on the condenser lens 107. The condenser lens 107 condenses the excitation light to provide a light spot, having a selected size, on the bio-chip 130. At this point, according to an embodiment, the size of the light spot is sufficiently large to illuminate the entire bio-chip 130. Therefore, the entire bio-chip 130 may be excited with a single illumination of excitation light instead of dividing the bio-chip 130 into a plurality of sections and sequentially scanning each of the sections. Although the condenser lens 107 is roughly shown as a single lens device in FIG. 1, the condenser lens 107 may also comprise a lens group including a plurality of lenses. Generally, an outer region of a light spot of light condensed by the condenser lens 107 is more affected by aberration and is distorted more significantly as compared to a center region thereof. Thus, a light spot with a size several times greater than the size of the bio-chip 130 (more particularly, the size of an array of gene spots disposed on the bio-chip 130) may be formed and only a center region of the light spot, where distortion is relatively insignificant, may be used. Furthermore, according to an embodiment, an aspheric lens may be used as the condenser lens 107 to eliminate spherical aberration, etc. If the condenser lens 107 is comprises a lens group including a plurality of lenses, at least one of the lenses in the lens group may be an aspheric lens.

Accordingly, when the bio-chip 130 is illuminated by the excitation light, a fluorescent material attached to a sample gene, which is combined with a gene spot within the bio-chip 130, is excited and emits a fluorescent light. The fluorescent light is desirably detected by the fluorescent light detecting system further disclosed above. In an embodiment as illustrated in FIG. 1, the bio-chip 130 is disposed on an opaque or reflective substrate. Therefore, the fluorescent light emitted by the fluorescent material passes through the condenser lens 107 and travels along the optical axis OX toward the polarizing beam splitter 105. At this point, the fluorescent light is in the unpolarized state, thus without a specific polarization, and the polarizing beam splitter 105 functions as a half mirror with respect to the fluorescent light. Therefore, a part of fluorescent light is reflected by the polarizing beam splitter 105 and travels toward the excitation light absorbing filter 110, which constitutes a part of the fluorescent light detecting system. The excitation light absorbing filter 110 may be disposed to face the fluorescent light outputting surface of the polarizing beam splitter 105.

In an embodiment, a part of the excitation light, which illuminates the bio-chip 130, is reflected by the bio-chip 130 and passes the λ/4 plate 106 again. At this point, the excitation light is converted to a light of P-polarization by the λ/4 plate 106. Then, the excitation light of P-polarization may be reflected by the polarizing beam splitter 105 and incident to the excitation light absorbing filter 110. In the current embodiment, light to be detected by the optical detector 113 is only fluorescent light. The intensity of excitation light is greater than that of fluorescent light, thus may interrupt precise measurement. The excitation light absorbing filter 110 transmits substantially only fluorescent light and absorbs incident excitation light, and may be a wavelength selective filter, for example. When the λ/4 plate 106 is not used in an embodiment, fluorescent light is partially reflected on the polarizing beam splitter 105 and is directed to the optical detector 113. In contrast, the incident excitation light is reflected back to the light source 101 transmitting through the polarizing beam splitter 105, which may induce instability or damage to the light source 101. However, these problems can be avoided if the reflected excitation light on the bio-chip 130 is diverged or not directed to the light source 101, and in the excitation light to the excitation light absorbing filter 110 may be reduced. Therefore, in another embodiment, the λ/4 plate 106 may be omitted.

The deformable mirror 111, the projection optical system 112 and the optical detector are sequentially disposed after the excitation light absorbing filter 110. Fluorescent light, having passed through the excitation light absorbing filter 110, is reflected by the deformable mirror 111, and forms an image on the optical detector 113 via the projection optical system 112. At this point, a fluorescent image formed on the optical detector 113 may be distorted due to the uneven surface of the bio-chip 130 and an aberration of an optical device on the light path between the bio-chip 130 and the optical detector 113. The deformable mirror 111 and the projection optical system 112 may perform a correction of a distortion in image of the fluorescent light.

The deformable mirror 111 is a mirror wherein the reflective surface is freely deformable by mechanical or electrical manipulation. For example, the reflective surface of the deformable mirror 111 may comprise a flexible material, and an electrical or a mechanical device for deforming the flexible reflective surface, for example by partially pushing or pulling the flexible reflective surface, may be arranged as a two-dimensional array under the reflective surface. Thus, an aberration can be intentionally provided to the reflective surface of the deformable mirror 111 to compensate for an aberration existing on the light path between the bio-chip 130 and the deformable mirror 111. For example, a spherical aberration may be compensated by providing a spherical aberration opposite to spherical aberrations accumulated along the light path between the bio-chip 130 and the deformable mirror 111. Accordingly, a distortion in a fluorescent image may be corrected by the deformable mirror 111.

The fluorescent light is incident on the projection optical system 112 after most of the distortion in a fluorescent image is corrected by the deformable mirror 111. The projection optical system 112 may comprise a plurality of lenses to provide a fluorescent image to the optical detector 113 without additional aberration. Although only an imaging lens 112a and a projection lens 112b are shown in FIG. 1, more lenses may be disposed in the projection optical system 112. The lens of the projection optical system 112 may be an aspheric lens with reduced aberration. However, the reflective surface of the deformable mirror 111 may also be deformed in consideration of an aberration of the projection optical system 112. For example, by analyzing a fluorescent image detected by the optical detector 113, the reflective surface of the deformable mirror 111 may also be continuously deformed until the fluorescent image detected by the optical detector 113 has a selected or minimal level of distortion.

An image of fluorescent light incident on the optical detector 113 is converted to an electrical signal by the optical detector 113 and the signal is transmitted to an image signal processing unit 140, such as a computer. The optical detector 113 may comprise between about 10 and about 1,000,000,000 pixels, specifically between about 1000 and about 10,000,000 pixels, more specifically between about 100,0000 and about 1,000,000 pixels, which can disposed in an array, to detect a fluorescent image with respect to all gene spots within the bio-chip 130 at once. For example, the optical detector 113 may be a photo multiplier tube ("PMT"), a charge-coupled device ("CCD"), or complementary metal-oxide semiconductor ("CMOS") image sensor ("CIS"), or the like or a combination thereof.

Figure 3A:
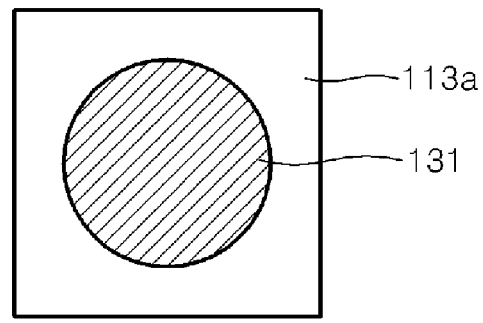
FIGS. 3A and 3B are diagrams illustrating an exemplary embodiment of a matching state between a pixel of an optical detector used in the optical detecting apparatus for a bio-chip of FIG. 1 and a corresponding gene spot in a bio-chip.
Figure 3B:
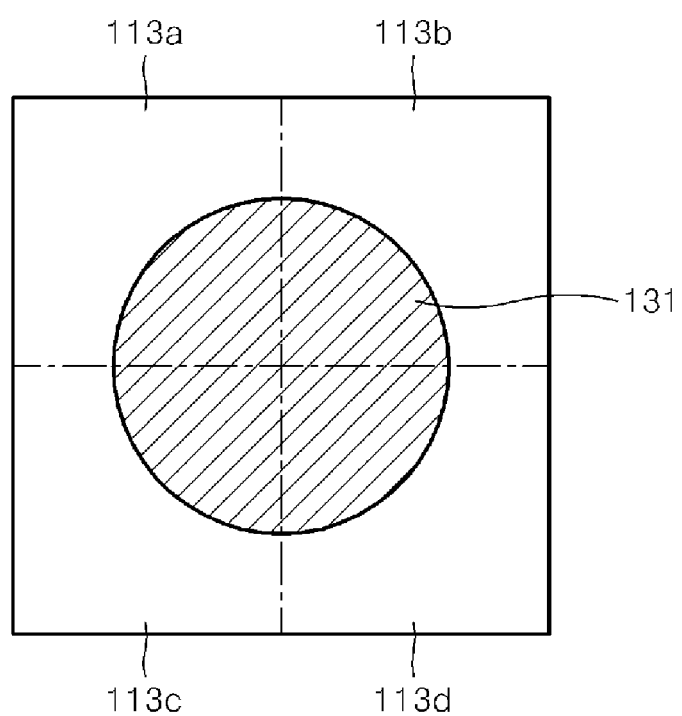

Each pixel of the optical detector 113 is desirably matched to a plurality of gene spots within the bio-chip 130. For example, as shown in FIG. 3A, a single pixel 113a of the optical detector 113 may be matched to an image 131 of a single gene spot within the bio-chip 130, thus may be matched one-to-one. However, to obtain more reliable data, an image of a single gene spot may be matched to n (wherein n is a natural integer) pixels of the optical detector 113. FIG. 3B is a diagram of an example in which an image 131 of a single gene spot is matched to four pixels 113a through 113d. In this embodiment, the four pixels 113a through 113d may detect intensity of the image 131 of a single gene spot together, and thus detection error may further be reduced. According to another embodiment, the magnification of the projection optical system 112 described above may be adjusted to freely adjust a matching ratio between pixels of the optical detector 113 and images of gene spots within the bio-chip 130. For example, the projection optical system 112 may be a zoom lens system, which has a variable magnification and is capable of zooming to obtain a selected image.

In addition, to obtain data with improved reliability, an image of each gene spot may be more precisely aligned to a corresponding pixel of the optical detector 113. The alignment may be performed by a stage 120 supporting the bio-chip 130. Furthermore, according to an embodiment, elements of the optical system other than the bio-chip 130, such as the deformable mirror 111, the optical detector 113 or the like may also be disposed on a stage. The stage 120 is designed to move in two horizontal perpendicular directions, such as a Y-axis direction and a Z-axis direction, as is shown in FIG. 1, for example, to precisely locate an image of a gene spot on a corresponding pixel. Furthermore, the stage 120 may also be designed to move in the vertical direction, that is an X-axis direction as shown in FIG. 1, for improved focusing of the condenser lens 107. The stage 120 may also be tilted with respect to the X-, Y- or Z-axis. Furthermore, the bio-chip 130 and the optical detector 113 may be rotated or tilted with respect to each other. For example, the stage 120 may rotate around the X-axis to correct relative rotation between the bio-chip 130 and the optical detector 113. Tilt of the bio-chip 130 may be corrected as the stage 120 rotates around the Y-axis and the Z-axis.

Figure 4:
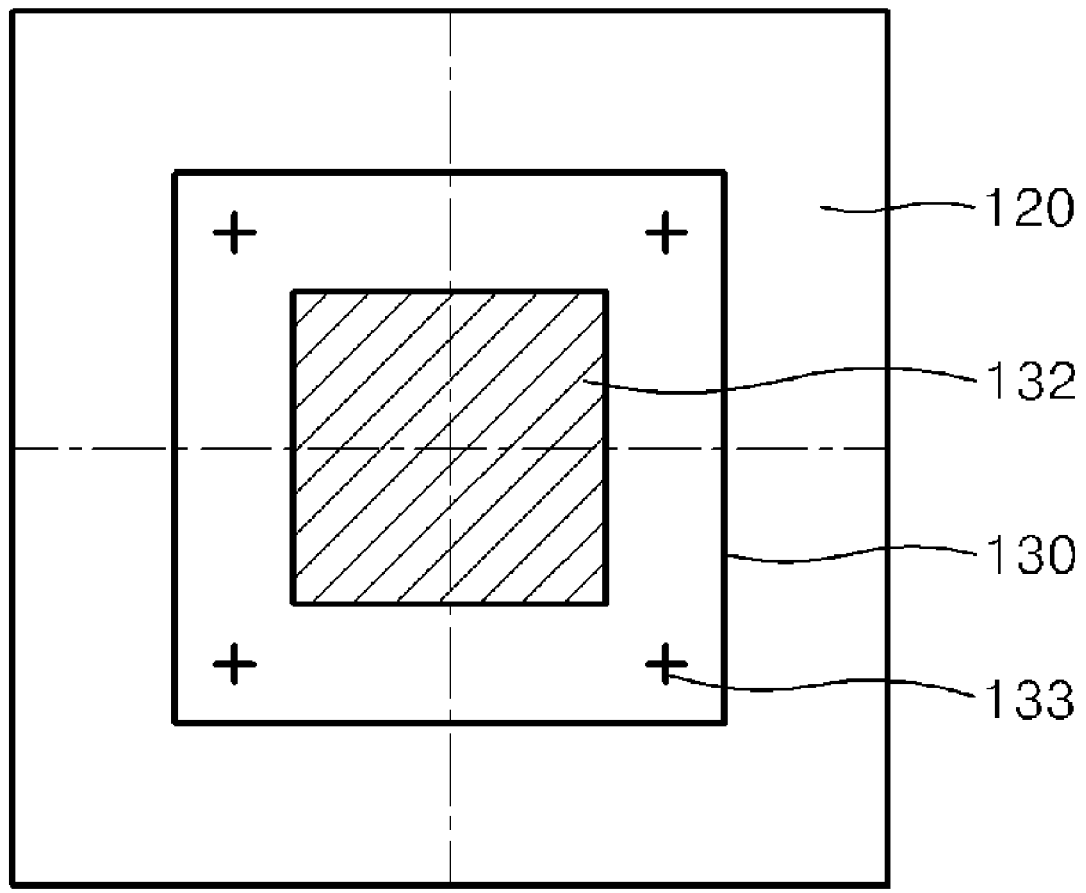
FIG. 4 illustrates an exemplary embodiment of an array of gene spots on a top surface of a bio-chip and an alignment mark.

The bio-chip 130 may include an alignment mark having a selected shape for to improve alignment of the bio-chip 113 with the optical detector 113 when the stage 120 is moved in a straight line or rotated as describe above. For example, as shown in FIG. 4, a plurality of alignment marks 133 may be disposed outside a gene spot array 132 on a top surface of the bio-chip 130. Thus, an alignment status of the bio-chip 130 may be determined by analyzing the alignment marks 133 detected by the optical detector 113. Although the shape of the alignment marks 133 is a cross in FIG. 4, the alignment marks 133 may have various shapes. Furthermore, the alignment marks 133 may also be disposed inside the gene spot array 132.

According to an embodiment, a fluorescent image of the entire bio-chip 130 without distortions may be obtained with a single illumination of an excitation light, because a distortion in a fluorescent image can be sufficiently corrected by using the deformable mirror 111. Thus, the bio-chip 130 may be read and analyzed with improved rapidity. In particular, since the reflective surface of the deformable mirror 111 may be freely deformed, a distortion in the image due to an uneven surface of the bio-chip 130 may be compensated for. Therefore, the bio-chip 130 is not limited to a bio-chip having a highly flat and even surface, rather the bio-chip 130 can have a modulated or uneven surface. Furthermore, because the bio-chip 130 can be read with improved rapidity, thus in less time, data reliability may be further improved by reading the same bio-chip 130 a plurality of times and determining an average thereof. Furthermore, an optical system may be further simplified by not having to use a device for precisely scanning the bio-chip 130. Thus, the optical detecting apparatus 100 may be miniaturized, and cost of manufacturing the same may be reduced. Therefore, a portable optical detecting apparatus for a bio-chip may be provided.

Figure 5:
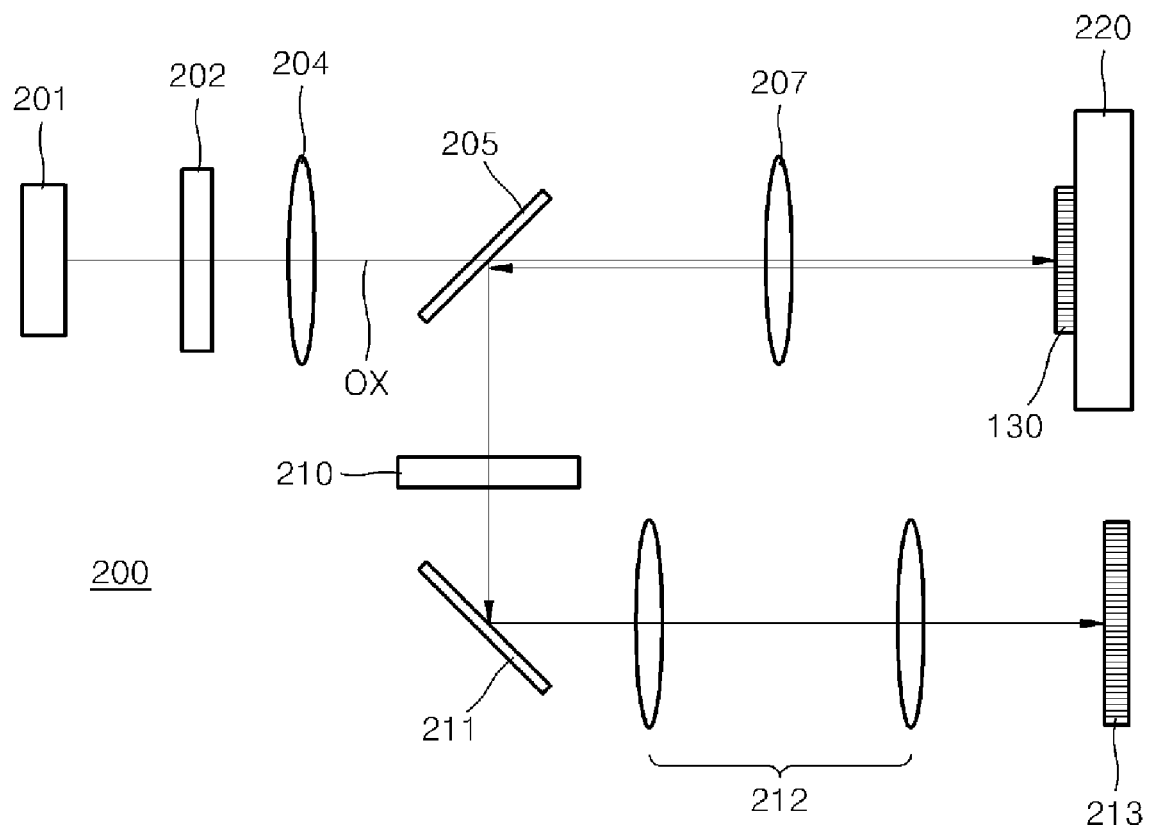
FIG. 5 is a diagram schematically showing another exemplary embodiment of an optical detecting apparatus for a bio-chip.

FIG. 5 is a diagram schematically showing a configuration of another exemplary embodiment of an optical detecting apparatus 200 for a bio-chip. A difference between the optical detecting apparatus 100 shown in FIG. 1 and the optical detecting apparatus 200 shown in FIG. 5 is that a dichromic mirror 205 is used for altering a light path instead of the polarizing beam splitter 105. In the embodiment of FIG. 5, since the polarizing beam splitter 105 is not used, a polarizer and a $\lambda/4$ plate are also not necessary. The optical detecting apparatus 200 shown in FIG. 5 is otherwise identical to the optical detecting apparatus 100 shown in FIG. 1. Configuration and operation of a light source 201, a light diffusing device 202, a collimating lens 204, a condenser lens 207, an excitation light absorbing filter 210, a deformable mirror 211, a projection optical system 212, an optical detector 213 and a stage 220 may be the same as their equivalents shown in FIG. 1. In other words, the light source 201, the light diffusing device 202, the collimating lens 204, and the condenser lens 207 form a light source system for illuminating the bio-chip 130 as in the previous embodiment. Furthermore, the excitation light absorbing filter 210, the deformable mirror 211, the projection optical system 212 and the optical detector 213 form a fluorescent light detecting system as in the previous embodiment.

The dichromic mirror 205 may be, for example, a wavelength selective mirror, which reflects light of a wavelength corresponding to the wavelength of fluorescent light emitted by the bio-chip 130 and transmits light of other wavelengths. Thus, excitation light emitted by the light source 201 may pass through the dichromic mirror 205 and reach the bio-chip 130. Furthermore, fluorescent light emitted by the bio-chip 130 may be reflected by the dichromic mirror 205 and directed to the optical detector 213. In this regard, the dichromic mirror 205 may be considered as a light path altering device. However, in an embodiment, the dichromic mirror 205 may be configured to transmit light of a wavelength corresponding to the wavelength of fluorescent light emitted by the bio-chip 130 and reflect light of other wavelengths. In this case, instead of the condenser lens 207, the bio-chip 130 and the stage 220, the excitation light absorbing filter 210, the deformable mirror 211, the projection optical system 212 and the optical detector 213 will be disposed on the optical axis OX.

Figure 6:
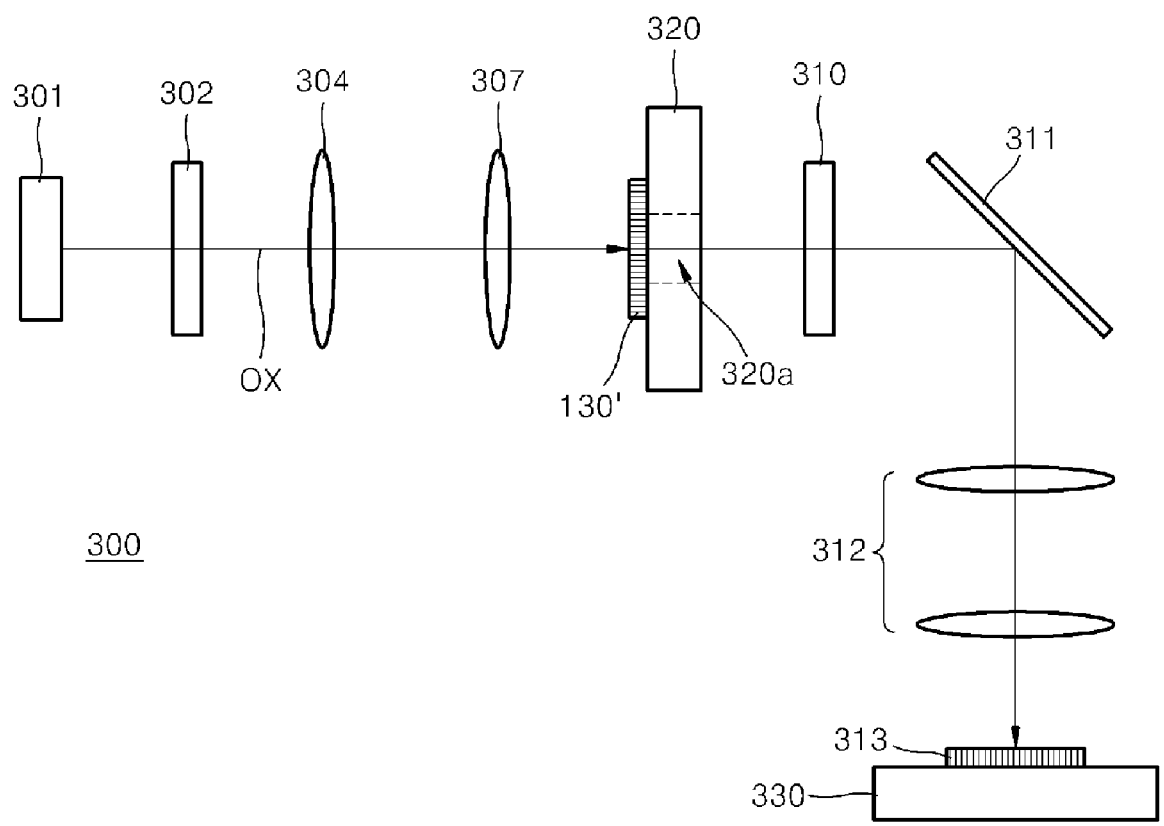
FIG. 6 is a diagram schematically showing another exemplary embodiment of an optical detecting apparatus for a bio-chip.

FIG. 6 is a diagram schematically showing a configuration of another exemplary embodiment of an optical detecting apparatus 300 for a bio-chip. In the embodiment of FIG. 6, a bio-chip 130' is disposed on a transparent substrate. Thus, a fluorescent light emitted by the bio-chip 130' may travel through the bio-chip 130'. As compared to the embodiment of FIG. 1, and as shown in FIG. 6, a light source system for illuminating a bio-chip and a fluorescent light detecting system are disposed on the opposite sides of the bio-chip 130'. Thus, the embodiment shown in FIG. 6 can operate without a light path altering unit. In other words, in the embodiment shown in FIG. 6, either the polarizer 103, the polarizing beam splitter 105 and the λ/4 plate 106 shown in FIG. 1, or the dichromic mirror 205 shown in FIG. 5 may be omitted in the optical detecting apparatus 300 for a bio-chip. Instead, an excitation light absorbing filter 310 directly faces a surface of the bio-chip 130', which is opposite to a surface of the bio-chip 130' illuminated by the excitation light.

Configuration and operation of a light source system and a fluorescent light detecting system may be otherwise identical to the embodiment of FIG. 1. For example, a light source 301, a light diffusing device 302, a collimating lens 304 and a condenser lens 307 may be identical to the light source 101, the light diffusing device 102, the collimating lens 104 and the condenser lens 107 of FIG. 1, respectively. Furthermore, the excitation light absorbing filter 310, a deformable mirror 311, a projection optical system 312 and an optical detector 313 may be identical to the excitation light absorbing filter 110, the deformable mirror 111, the projection optical system 112 and the optical detector 113 of FIG. 1, respectively. However, in the embodiment of FIG. 6, the light source 301, the light diffusing device 302, the collimating lens 304, the condenser lens 307, the excitation light absorbing filter 310, the deformable mirror 311, the projection optical system 312 and the optical detector 313 may be disposed on the same optical axis OX bent by the deformable mirror 311.

In addition, the bio-chip 130' and the optical detector 313 may be supported and rotated by first and second stages 320 and 330, respectively. Either an aperture or a transparent window 320a may be disposed in the first stage 320, which may support the bio-chip 130', such that the fluorescent light emitted by the bio-chip 130' can pass therethrough. The size of the aperture or the transparent window 320a may be the same as or larger than that of an array of gene spots disposed on the bio-chip 130', for example. The second stage 330 supporting the optical detector 313 may be identical to the first stage 320 supporting the bio-chip 130'. However, in an embodiment, only one of the first and second stages 320 and 330 may be used.

Figure 7:
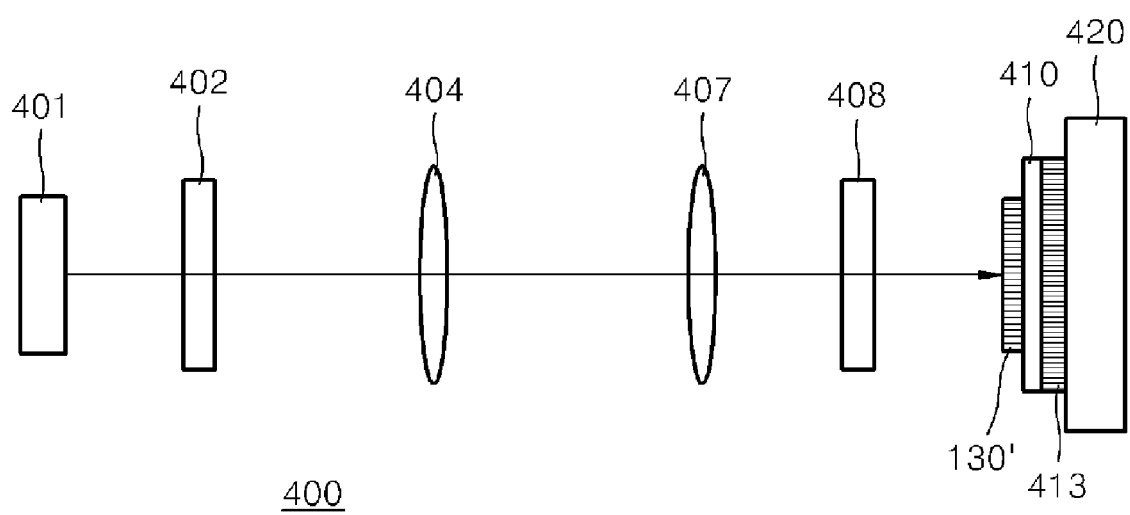
FIG. 7 is a diagram schematically showing another exemplary embodiment of an optical detecting apparatus for a bio-chip.

FIG. 7 is a diagram schematically showing a configuration of an exemplary embodiment of an optical detecting apparatus 400 for a bio-chip. In the embodiment of FIG. 7, the bio-chip 130' is disposed on a transparent substrate as in the embodiment of FIG. 6. As a result, the fluorescent light emitted by the bio-chip 130' may travel through the bio-chip 130'. Therefore, as in the embodiment of FIG. 6, a light source system for illuminating a bio-chip and a fluorescent light detecting system may be disposed on the opposite sides of the bio-chip 130'. Therefore, the optical detecting apparatus 400 can operate without a light path altering unit. Thus, in the embodiment shown in FIG. 7, either the polarizer 103, the polarizing beam splitter 105 and the λ/4 plate 106 shown in FIG. 1, or the dichromic mirror 205 shown in FIG. 5 may be omitted from the optical detecting apparatus 400 for a bio-chip.

Configuration and operation of a light source system in the optical detecting apparatus 400 according to the embodiment of FIG. 7 may be identical to those in the embodiment of FIG. 1. For example, a light source 401, a light diffusing device 402, a collimating lens 404 and a condenser lens 407 may be identical to the light source 101, the light diffusing device 102, the collimating lens 104 and the condenser lens 107 of FIG. 1, respectively. However, to substantially prevent or eliminate a distortion in the fluorescent image, an aberration compensating device 408 may be further disposed between the condenser lens 407 and the bio-chip 130', for example. Thus the aberration compensation device 408 may have the same function as the deformable mirror 111. The aberration compensation device 408 may be a transmissive device, and may not be a reflective device.

In addition, according to the current embodiment, a fluorescent light detecting system may comprise an excitation light absorbing filter 410 and an optical detector 413. In an embodiment, a fluorescent light detecting system may consist essentially of an excitation light absorbing filter 410 and an optical detector 413. In another embodiment, a fluorescent light detecting system may consist of an excitation light absorbing filter 410 and an optical detector 413. In particular, the excitation light absorbing filter 410 and the optical detector 413 may be integrated to the bio-chip 130' as a single body and fixed on a surface of the bio-chip 130', which is a surface opposite to a surface of the bio-chip 130' illuminated by the excitation light. To improve alignment of a pixel of the optical detector 413 with respect to a corresponding gene spot within the bio-chip 130', the optical detector 413 and the bio-chip 130' may be aligned in advance and fixed together such that the optical detector 413 and the bio-chip 130' do not substantially move with respect to each other. The bio-chip 130', the excitation light absorbing filter 410 and the optical detector 413, which may be affixed to form a single body as described above, may be supported by a single stage 420 and may be moved to a region optimally illuminated by the light source system. In an embodiment, it may be advantageous to adjust the condenser lens 407 of the light source system to have a deep depth of focus such that at least an entire region from the bio-chip 130' to the optical detector 413 is focused.

According to the embodiment of FIG. 7, a fluorescent light detecting system does not require expensive components, such as a deformable mirror and a projection optical system, and thus a cost of manufacturing an optical detecting apparatus for a bio-chip may further be reduced. Furthermore, alignment of components during assembly of an optical detecting apparatus for a bio-chip may be facilitated due to a reduced number of components. Furthermore, since the length of a light path in a fluorescent light detecting system is shortened, the size of an optical detecting apparatus for a bio-chip may be further reduced.

It should be understood that the exemplary embodiments described herein should be considered in a descriptive sense only and not for purposes of limitation. Descriptions of features or aspects within each embodiment should typically be considered as available for other similar features or aspects in other embodiments. For example, although the optical systems described in conjunction with the above embodiments above are refraction optical systems comprising lenses, similar or the same effects may be obtained by using a reflection optical system including concave mirrors, convex mirrors or flat mirrors.

What is claimed is:

1. An optical detecting apparatus for a bio-chip, the optical detecting apparatus comprising:
    a light source system for illuminating a bio-chip with an excitation light, wherein the light source system comprises a light source for the excitation light, a light diffusing device, and a condenser lens or a condenser mirror, which are sequentially disposed on a same optical axis and in a direction in which the excitation light travels;
    a fluorescent light detecting system for detecting a fluorescent light emitted by the bio-chip; and
    a light path altering unit for directing the excitation light emitted by the light source system to a bio-chip and directing the fluorescent light emitted by the bio-chip to the fluorescent light detecting system which detects a fluorescent image of the entire biochip with a single illumination of excitation light, wherein the light path altering unit comprises a polarizing beam splitter disposed between the light diffusing device and the condenser lens or the condenser mirror, a polarizer disposed between the light diffusing device and the polarizing beam splitter, and a quarter-wave plate disposed between the polarizing beam splitter and the condenser lens or the condenser mirror;
    wherein a cross-sectional area of the excitation light irradiated by the light source system onto the bio-chip is greater than an entire area of the bio-chip.

2. The optical detecting apparatus of claim 1, wherein the fluorescent light detecting system comprises an excitation light absorbing filter, a deformable mirror, a projection optical system and an optical detector, which are sequentially disposed in a direction in which the fluorescent light travels, and
    the excitation light absorbing filter is disposed to face a fluorescent light outputting surface of the polarizing beam splitter.

3. The optical detecting apparatus of claim 2, wherein the deformable mirror comprises a reflective surface, which can be deformed by mechanical or electrical manipulation to correct for a distortion in the fluorescent image.

4. The optical detecting apparatus of claim 2, wherein the projection optical system is a zoom lens system or a zoom mirror system, having variable magnification.

5. The optical detecting apparatus of claim 2, wherein the optical detector comprises an array of pixels, and comprises a photo multiplier tube, a charge-coupled device, a complementary metal-oxide semiconductor image sensor or a combination thereof.

6. The optical detecting apparatus of claim 5, wherein an image of a single gene spot within a bio-chip is matched to at least one of the pixels of the optical detector.

7. The optical detecting apparatus of claim 1, further comprising a stage for supporting, moving, tilting and rotating the bio-chip.

* * * * *